US00PP31603P2

(12) United States Plant Patent
Kordes

(10) Patent No.: US PP31,603 P2
(45) Date of Patent: Mar. 31, 2020

(54) HYBRID TEA ROSE PLANT NAMED 'KORBROCAZE'

(50) Latin Name: *Rosa hybrida*
Varietal Denomination: KORbrocaze

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/999,298

(22) Filed: Aug. 29, 2018

(30) Foreign Application Priority Data

Sep. 20, 2017 (QZ) ..... PBR 20172301

(51) Int. Cl.
*A01H 5/02* (2018.01)
*A01H 6/74* (2018.01)

(52) U.S. Cl.
USPC ..... Plt./136
CPC ..... *A01H 6/749* (2018.05)

(58) Field of Classification Search
USPC ..... Plt./136
See application file for complete search history.

(56) References Cited

U.S. PATENT DOCUMENTS

PP21,284 P3 * 9/2010 Meilland ..... Plt./136

* cited by examiner

*Primary Examiner* — Anne Marie Grunberg
(74) *Attorney, Agent, or Firm* — Buchanan Ingersoll & Rooney PC

(57) ABSTRACT

A new and distinct variety of hybrid tea rose plant, herein referred to by its cultivar name, 'KORbrocaze', is provided which forms in abundance on a substantially continuous basis attractive, creamy apricot colored blossoms. The vegetation is vigorous and the growth habit is very bushy and upright. Attractive ornamental glossy, dark green foliage is formed. The new variety is particularly well suited for providing distinctive ornamentation in the landscape.

4 Drawing Sheets

Figure 1:
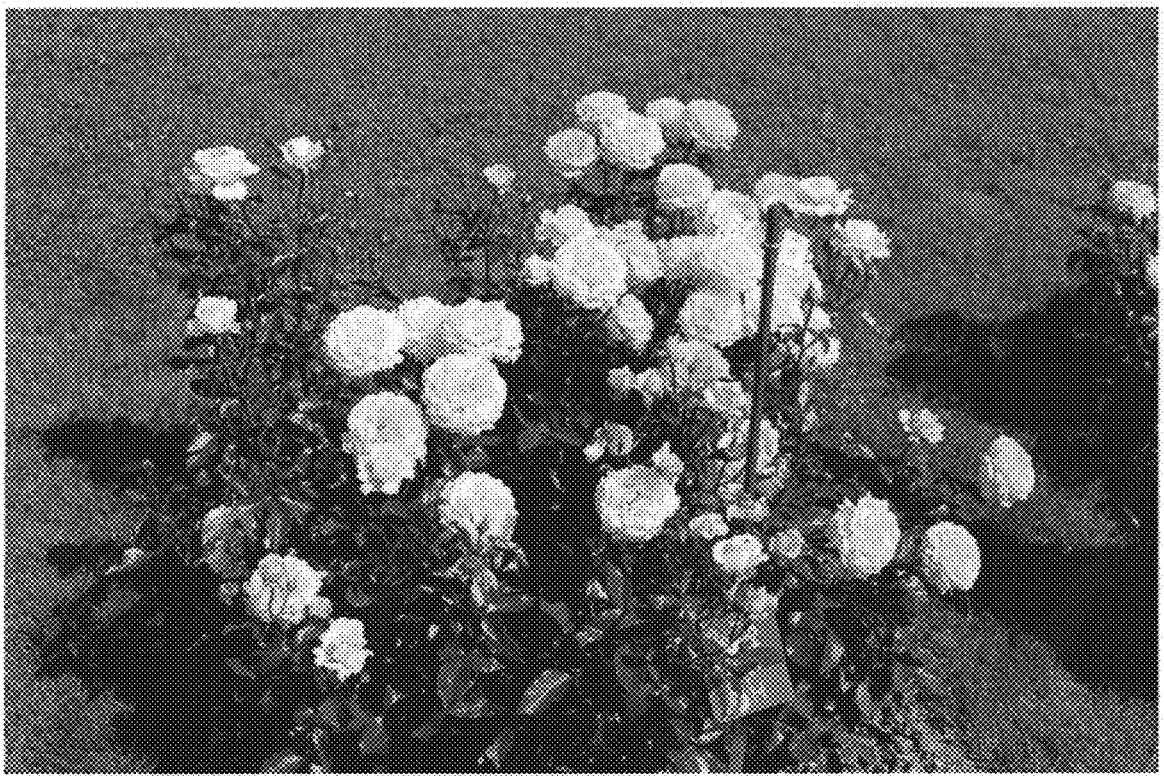

Botanical/commercial classification: Latin name—*Rosa hybrida. Common name*.—Hybrid Tea Rose Plant.
Varietal denomination: 'KORbrocaze'.

CROSS-REFERNCE TO RELATED APPLICATIONS

This application claims priority to Plant Breeders' Right Application Number 20172301, which was filed in the European Union on Sep. 20, 2017, the contents of which are hereby expressly incorporated by reference in their entirety for all purposes.

SUMMARY OF THE INVENTION

The new variety of *Rosa hybrida* hybrid tea rose plant of the present invention was created during May 2008 at Offenseth-Sparrieshoop, Germany by artificial pollination wherein two parents were crossed which previously had been studied in the hope that they would contribute the desired characteristics. The female parent (i.e., seed parent) of the new variety was the 'ADAterhuit' variety (non-patented in the United States). The male parent (i.e., pollen parent) of the new variety was an unnamed seedling from a previous cross of an unnamed seedling and the 'MACgenev' variety (non-patented in the United States).

The parentage can be summarized as follows:
'ADAterhuit' x (unnamed seedling x 'MACgenev')

The seeds resulting from the above pollination were sown and small plants were obtained which were physically and biologically different from each other. Selective study resulted in the identification of a single plant of the new variety.

It was found that the new hybrid tea rose plant of the present invention possesses the following combination of characteristics:

(a) abundantly and substantially continuously forms attractive, creamy apricot colored blossoms,
(b) exhibits a very bushy and upright growth habit,
(c) forms vigorous vegetation, and
(d) forms attractive ornamental glossy, dark green foliage.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'ADAterhuit' variety (i.e., seed parent) exhibits a different flower shape, a different flower color, and a lower level of disease resistance compared to the new variety. Additionally, the (unnamed seedling x 'MACgenev') variety (i.e., pollen parent) exhibits a different flower color, lower petal count, and a higher level of disease resistance compared to the new variety. Moreover, the new variety can be readily distinguished from non-parental related similar varieties. For example, the 'ORAclelon' variety (U.S. Plant Pat. No. 21,577) exhibits larger diameter flowers with lower number of petals compared to the new variety The new variety has been found to undergo asexual propagation in Klein Offenseth-Sparrieshoop, Germany by a number of routes such as budding. Asexual propagation techniques in Germany have shown that the characteristics of the new variety are homogeneous, stable, and strictly transmissible by such asexual propagation from one generation to another. Accordingly, the new variety undergoes asexual propagation in a true-to-type manner.

The new variety has been named 'KORbrocaze'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately three years of age and was observed at Baden-Baden, Germany in July, 2017 while growing outdoors on understock.

FIG. 1—illustrates a specimen of a plant displaying floral buds and flowers at varying points of opening.

Figure 2:
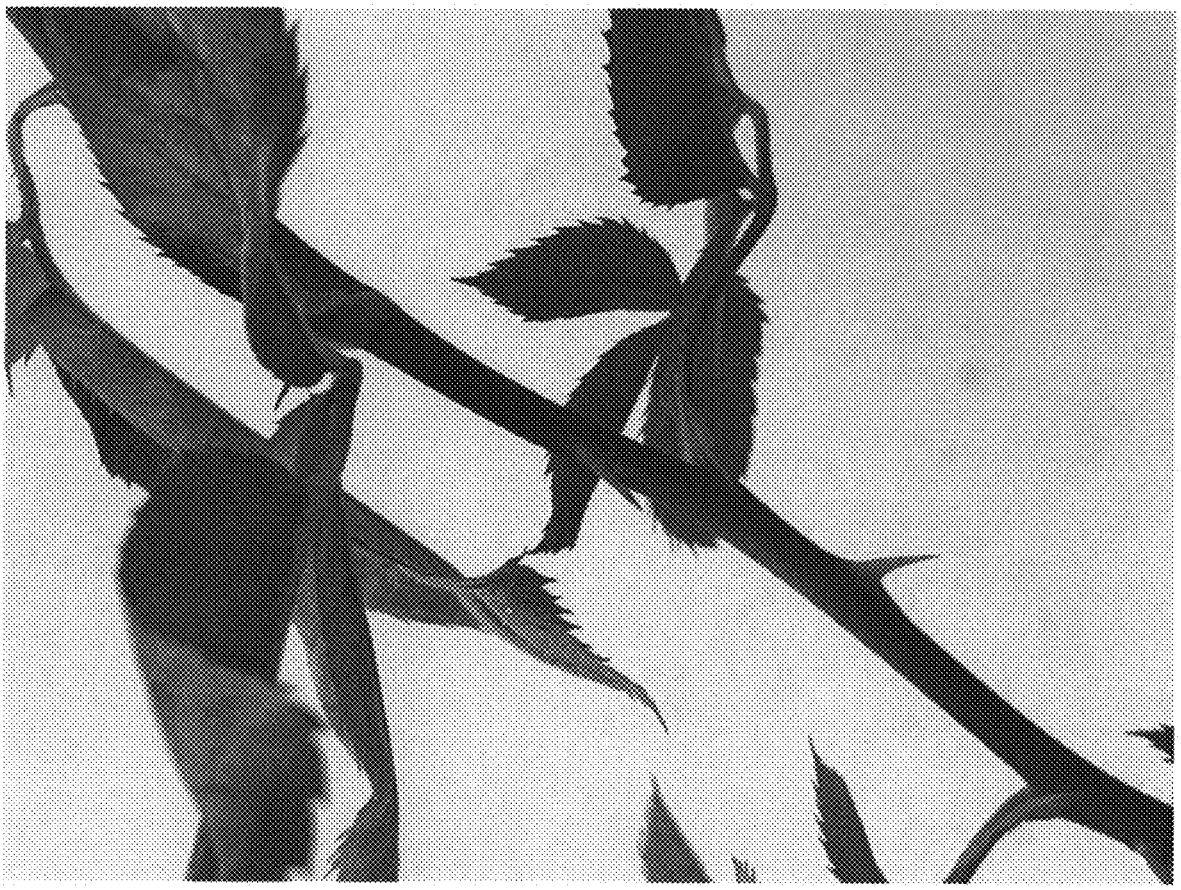

FIG. 2—illustrates a stem of the new variety displaying the leaves and prickles.

Figure 3:
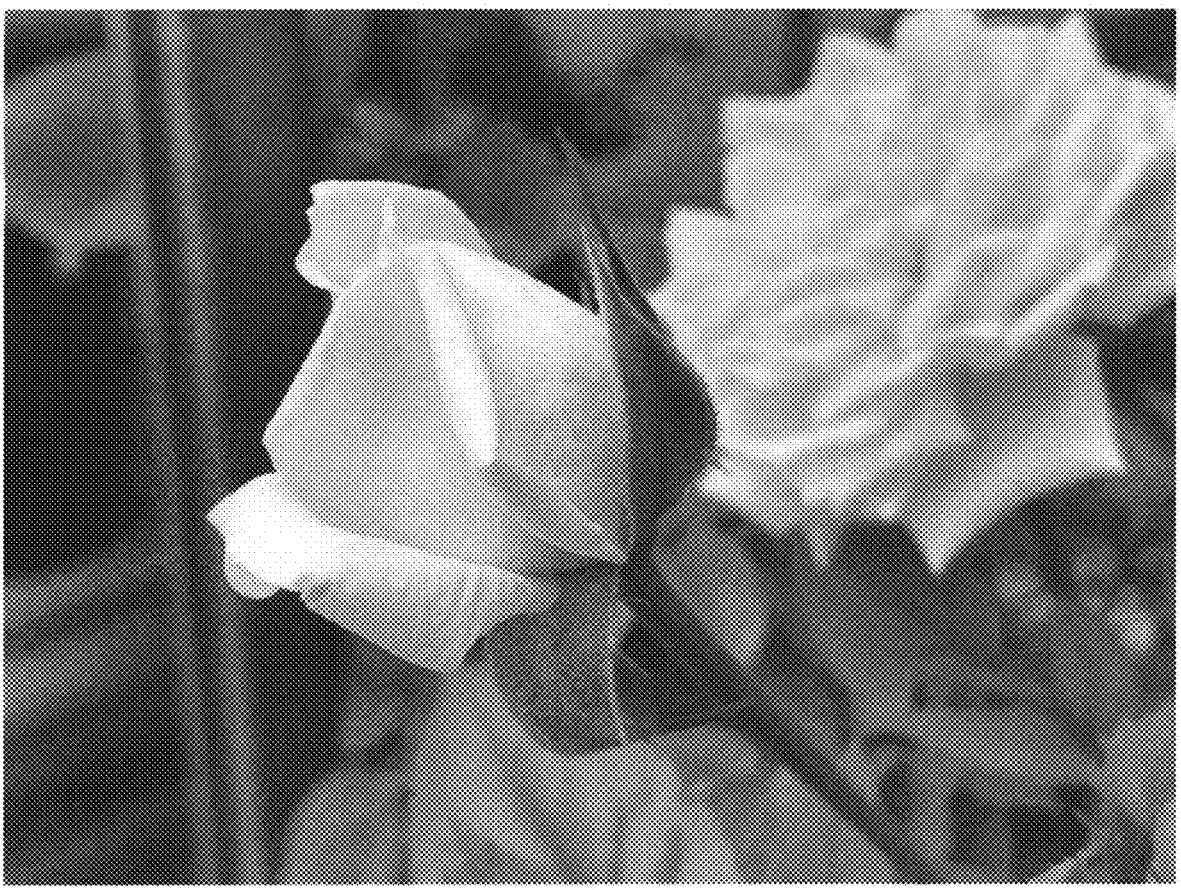

FIG. 3—illustrates a bud of the new variety.

Figure 4:
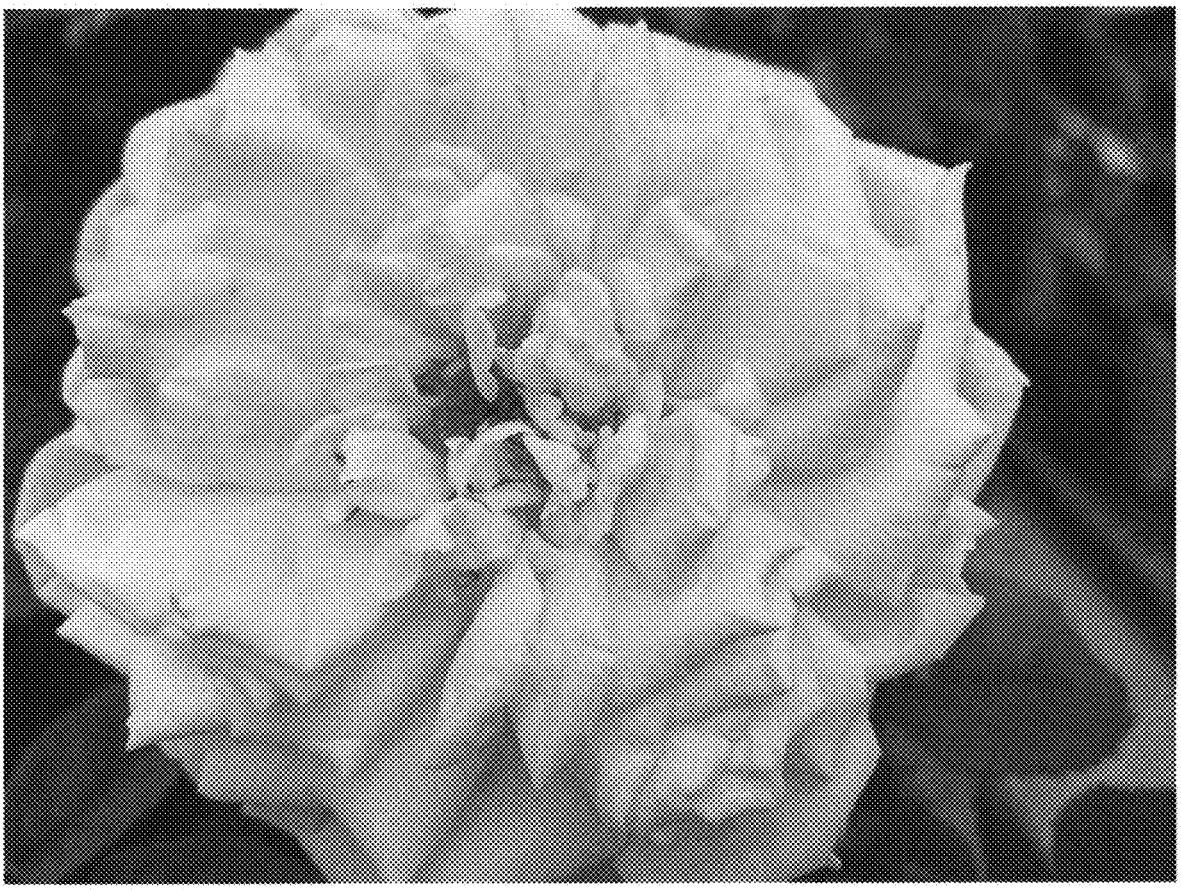

FIG. 4—illustrates an open flower of the new variety.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a two-year-old specimen of the new variety, observed during May, while growing in a one-gallon container on its own roots at Cochranville, Pa.

Class: Hybrid Tea Rose Plant.

Plant:

*Habit.*—Very bushy and upright.

*Height.*—Approximately 45.0 cm on average from the top of the soil plane.

*Width.*—Approximately 40.0 cm on average.

Branches:

*Young stem color.*—Commonly near Green Group 143B.

*Old wood color.*—Commonly near Green Group 143A.

*Main stem length.*—Approximately 45.0 cm on average.

*Secondary stem length.*—Approximately 10.0 cm on average.

*Thorns.*—Young thorns: length is approximately 5.0 mm on average, width is approximately 2.0 mm at point of attachment on average, and color is commonly near Green Group 143C. — Old thorns: length is approximately 7.0 mm on average, width is approximately 3.0 mm at point of attachment on average, and color is commonly near Greyed-Brown Group N199B.

Foliage:

*General appearance.*—Ornamental glossy, dark green foliage.

*Young foliage.*—Upper surface color: commonly near Green Group 1396 with indistinguishable venation. — Under surface color: commonly near Green Group 139C with indistinguishable venation.

*Old foliage.*—Upper surface color: commonly near Green Group 139A with indistinguishable venation. — Under surface color: commonly near Green Group 138A with venation of near Green Group 138B.

*Petioles.*—Upper surface: texture is smooth, color is commonly near Green Group 138A. — Under surface: texture is glandular with some small prickles, color is commonly near Green Group 138B.

*Rachis.*—Color: upper surface is commonly near Green Group 138A, under surface is commonly near Green Group 138B.

*Stipules.*—Length: approximately 9.0 mm on average. — Width: approximately 5.0 mm on average. — Margin: entire to erose. — Color: upper and lower surfaces are commonly near Green Group 138B.

*Leaf margin.*—Serrate.

*Leaf margin undulation.*—Moderate.

Leaflets:

*Number.*—3, 5, and 7.

*Shape.*—Ovate.

*Texture.*—Upper surface is smooth; under surface is smooth.

*Size.*—Terminal leaflet: length is approximately 6.5 cm on average and width is approximately 4.5 cm on average. — Lower leaflets: length is approximately 3.7 cm on average and width is approximately 2.2 cm on average. — 5-Leaflet leaf: length is approximately 14.0 cm on average and width is approximately 10.0 cm on average.

Inflorescence:

*Number of flowers.*—Approximately 4 open blooms on average on a plant at once.

*Number of blooms per stem.*—Typically 1 bloom per stem on average.

*Peduncle.*—Color: commonly Yellow-Green Group 144B. — Diameter: approximately 3.0 mm on average. — Length: approximately 6.0 cm on average. — Surface texture: glandular.

*Sepals.*—Number: commonly 5. — Upper surface color and texture: covered in short pubescence and color is commonly near Yellow-Green Group 144A. — Under surface color and texture: puberulent and color is commonly near Yellow-Green Group 144B. — Size: length is approximately 2.5 cm on average and width is approximately 1.2 cm on average. — Margin: entire with occasional extensions on two or three sepals measuring approximately 2.0 mm in length and approximately 1.0 mm in width.

*Bud.*—Shape: ovoid. — Size: length is approximately 2.5 cm on average; width is approximately 1.5 cm on average. — Color when opening: commonly near Orange-Red Group 35B.

*Flower.*—Creamy apricot colored. — Form: double, cuplike. — Profile: flat to slightly convex. — Diameter: approximately 10.0 cm on average. — Height: approximately 4.5 cm on average. — Duration: commonly on the plant approximately 5 to 7 days on average. — Color when first and fully open: upper and surfaces are commonly near Orange Group 27D with a basal spot of near Yellow Group 13D. — Color when fading: upper and under surfaces are commonly near Yellow Group 4D with a basal spot of near Yellow Group 4A. — Fragrance: very strong.

*Petal.*—Number: approximately 65 on average. — Drop: good. — Length: inner petals are approximately 3.5 cm on average and outer petals are approximately 4.5 cm on average. — Width: inner petals are approximately 2.0 cm on average and outer petals are approximately 3.0 cm on average. — Shape: overall shape is broadly obovate; apex is round; and base is cuneate. — Margin: entire. — Undulation: moderate.

*Petaloids.*—Number: approximately 10 per flower on average. — Color: upper and under surfaces are commonly near Orange Group 27D with a basal spot of near Yellow Group 13D. — Size: length is approximately 2.5 cm on average and width is approximately 1.5 mm on average. — Texture: smooth. — Margins: variable, entire to erose. — Shape: variable, oblong and mostly curving inward; apex is round, and base is cuneate.

*Stamen.*—Number: approximately 86 on average. — Anthers: number is about 86 and color is commonly near Greyed-Orange Group 163C with near Greyed-Orange Group 166B along the margins; length is approximately 2.0 mm on average; and shape is oval. — Filaments: length is approximately 7.0 mm on average and color is commonly near Greyed-Red Group 182D.

*Pistils.*—Arrangement separate and free. — Number: approximately 70 on average. — Style: color is mostly near Yellow-Green Group 150D at the base transitioning to Red Group 45D towards the apex, and length is less than 1.0 mm on average. — Stigma: color is commonly near Yellow-Orange Group 22A, diameter is typically less than 1.0 mm, and shape is fan shaped.

*Receptacle.*—Diameter is approximately 8.0 mm on average, shape is urn shaped, color is commonly near Yellow-Green Group 144A, and surface texture is smooth.

*Pollen.*—None observed.

*Hips/seed.*—None observed.

Development:

*Vegetation.*—Dark green, vigorous, and glossy.

*Blooming.*—Abundant and substantially continuous from spring through frost.

*Resistance to disease.*—Very good resistance is exhibited.

Plants of the 'KORbrocaze' variety have not been observed under all possible environmental conditions to date. Accordingly, it is possible that the phenotypic expression may vary somewhat with changes in light intensity and duration, cultural practices, and other environmental conditions.

I claim:

1. A new and distinct hybrid tea rose plant characterized by the following combination of characteristics:

(a) abundantly and substantially continuously forms attractive, creamy apricot colored blossoms, (b) exhibits a very bushy and upright growth habit, (c) forms vigorous vegetation, and (d) forms attractive ornamental glossy, dark green foliage; substantially as herein shown and described.

* * * * *